United States Patent
Northrop et al.

(10) Patent No.: US 9,072,874 B2
(45) Date of Patent: Jul. 7, 2015

(54) MEDICAL DEVICES WITH A HEAT TRANSFER REGION AND A HEAT SINK REGION AND METHODS FOR MANUFACTURING MEDICAL DEVICES

(75) Inventors: Clay Northrop, Salt Lake City, UT (US); Ted Layman, Park City, UT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 272 days.

(21) Appl. No.: 13/470,023

(22) Filed: May 11, 2012

(65) Prior Publication Data
US 2012/0289938 A1 Nov. 15, 2012

Related U.S. Application Data

(60) Provisional application No. 61/485,750, filed on May 13, 2011.

(51) Int. Cl.
*A61B 5/00* (2006.01)
*A61M 25/00* (2006.01)
*A61M 25/09* (2006.01)

(52) U.S. Cl.
CPC ............ *A61M 25/09* (2013.01); *Y10T 29/49826* (2015.01); *A61M 25/001* (2013.01); *A61M 2025/09108* (2013.01)

(58) Field of Classification Search
USPC .......... 600/585, 434, 431, 433, 435; 604/525, 604/527; 228/203
See application file for complete search history.

(56) References Cited

U.S. PATENT DOCUMENTS

| | | | |
|---|---|---|---|
| 1,553,227 | A | 9/1925 | Anton et al. |
| 1,866,888 | A | 7/1932 | Hawley |
| 2,275,827 | A | 3/1942 | Plensler |
| 2,413,805 | A | 1/1947 | Vickers |
| 2,441,166 | A | 5/1948 | Raspert |
| 2,561,890 | A | 7/1951 | Stoddard |
| 2,722,614 | A | 11/1955 | Fryklund |
| 2,857,536 | A | 10/1958 | Light |
| 2,864,017 | A | 12/1958 | Waltscheff |
| 2,871,793 | A | 2/1959 | Michie et al. |
| 3,249,776 | A | 5/1966 | Anderson et al. |

(Continued)

FOREIGN PATENT DOCUMENTS

| | | |
|---|---|---|
| EP | 0 215 173 | 3/1987 |
| EP | 0 377 453 | 7/1990 |

(Continued)

OTHER PUBLICATIONS

H.A. Rothbart, "Helical Compression Springs", Mechanical Design and Systems Handbook, 1964, p. 33-13 (one sheet).

*Primary Examiner* — Brian Szmal
(74) *Attorney, Agent, or Firm* — Seager, Tufte & Wickhem, LLC

(57) ABSTRACT

Medical devices and methods for making and using the same are disclosed. An example medical device may include a guidewire. The guidewire may include a core wire having a distal portion. A tubular member may be disposed over the distal portion. The tubular member may have a plurality of slots formed therein. The tubular member may have a distal section with a heat transfer region and a heat sink region. A solder tip member may be attached to the tubular member. The solder tip member may include a portion extending through the heat transfer region of the tubular member to the heat sink region.

13 Claims, 11 Drawing Sheets

(56) References Cited

U.S. PATENT DOCUMENTS

| | | |
|---|---|---|
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Wilson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,538,622 A | 9/1985 | Samson et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,228,453 A | 7/1993 | Sepetka |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,049 A | 11/1994 | Raman et al. |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,409,015 A | 4/1995 | Palermo |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |

(56) References Cited

U.S. PATENT DOCUMENTS

| | | | |
|---|---|---|---|
| 5,551,444 | A | 9/1996 | Finlayson |
| 5,554,139 | A | 9/1996 | Okajima |
| 5,562,619 | A | 10/1996 | Mirarchi et al. |
| 5,569,197 | A | 10/1996 | Helmus et al. |
| 5,569,200 | A | 10/1996 | Umeno et al. |
| 5,569,218 | A | 10/1996 | Berg |
| 5,571,073 | A | 11/1996 | Castillo |
| 5,573,520 | A | 11/1996 | Schwartz et al. |
| 5,584,821 | A | 12/1996 | Hobbs et al. |
| 5,599,326 | A | 2/1997 | Carter |
| 5,599,492 | A | 2/1997 | Engelson |
| 5,601,539 | A | 2/1997 | Corso, Jr. |
| 5,605,162 | A | 2/1997 | Mirzaee et al. |
| 5,605,543 | A | 2/1997 | Swanson |
| 5,622,184 | A | 4/1997 | Ashby et al. |
| 5,630,806 | A | 5/1997 | Inagaki et al. |
| 5,637,089 | A | 6/1997 | Abrams et al. |
| 5,656,011 | A | 8/1997 | Uihlein et al. |
| 5,658,264 | A | 8/1997 | Samson et al. |
| 5,664,580 | A | 9/1997 | Erickson et al. |
| 5,666,968 | A | 9/1997 | Imran et al. |
| 5,666,969 | A | 9/1997 | Urick et al. |
| 5,669,926 | A | 9/1997 | Aust et al. |
| 5,676,659 | A | 10/1997 | McGurk |
| 5,676,697 | A | 10/1997 | McDonald |
| 5,682,894 | A | 11/1997 | Orr et al. |
| 5,690,120 | A | 11/1997 | Jacobsen et al. |
| 5,720,300 | A | 2/1998 | Fagan et al. |
| 5,722,609 | A | 3/1998 | Murakami |
| 5,728,063 | A | 3/1998 | Preissman et al. |
| 5,741,429 | A | 4/1998 | Donadio, III et al. |
| 5,746,701 | A | 5/1998 | Noone |
| 5,769,830 | A | 6/1998 | Parker |
| 5,772,609 | A | 6/1998 | Nguyen et al. |
| 5,782,809 | A | 7/1998 | Umeno et al. |
| 5,788,653 | A | 8/1998 | Lorenzo |
| 5,788,654 | A | 8/1998 | Schwager |
| 5,788,707 | A | 8/1998 | Del Toro et al. |
| 5,792,124 | A | 8/1998 | Horrigan et al. |
| 5,797,856 | A | 8/1998 | Frisbie et al. |
| 5,800,454 | A | 9/1998 | Jacobsen et al. |
| 5,807,075 | A | 9/1998 | Jacobsen et al. |
| 5,807,249 | A | 9/1998 | Qin et al. |
| 5,810,885 | A | 9/1998 | Zinger |
| 5,813,996 | A | 9/1998 | St. Germain et al. |
| 5,827,225 | A | 10/1998 | Ma Schwab |
| 5,827,242 | A | 10/1998 | Follmer et al. |
| 5,833,632 | A | 11/1998 | Jacobsen et al. |
| 5,836,926 | A | 11/1998 | Peterson et al. |
| 5,843,050 | A | 12/1998 | Jones et al. |
| 5,843,244 | A | 12/1998 | Pelton et al. |
| 5,851,203 | A | 12/1998 | van Muiden |
| 5,895,378 | A | 4/1999 | Nita |
| 5,897,537 | A | 4/1999 | Berg et al. |
| 5,902,254 | A | 5/1999 | Magram |
| 5,902,290 | A | 5/1999 | Peacock, III et al. |
| 5,902,499 | A | 5/1999 | Richerzhagen |
| 5,904,657 | A | 5/1999 | Unsworth et al. |
| 5,906,618 | A | 5/1999 | Larson, III |
| 5,911,715 | A | 6/1999 | Berg et al. |
| 5,911,717 | A | 6/1999 | Jacobsen et al. |
| 5,916,177 | A | 6/1999 | Schwager |
| 5,916,178 | A | 6/1999 | Noone |
| 5,916,194 | A | 6/1999 | Jacobsen et al. |
| 5,931,830 | A | 8/1999 | Jacobsen et al. |
| 5,935,108 | A | 8/1999 | Katoh et al. |
| 5,947,940 | A | 9/1999 | Beisel |
| 5,951,539 | A | 9/1999 | Nita et al. |
| 5,955,640 | A | 9/1999 | Paludetto et al. |
| 5,971,975 | A | 10/1999 | Mills et al. |
| 5,980,471 | A | 11/1999 | Jafari |
| 5,997,487 | A | 12/1999 | Kolehmainen et al. |
| 6,001,068 | A | 12/1999 | Uchino et al. |
| 6,004,279 | A | 12/1999 | Crowley et al. |
| 6,007,478 | A | 12/1999 | Siess et al. |
| 6,014,919 | A | 1/2000 | Jacobsen et al. |
| 6,017,319 | A | 1/2000 | Jacobsen et al. |
| 6,022,343 | A | 2/2000 | Johnson et al. |
| 6,022,369 | A | 2/2000 | Jacobsen et al. |
| 6,024,730 | A | 2/2000 | Pagan |
| 6,027,461 | A | 2/2000 | Walker et al. |
| 6,042,553 | A | 3/2000 | Solar et al. |
| 6,045,547 | A | 4/2000 | Ren et al. |
| 6,048,339 | A | 4/2000 | Zirps et al. |
| 6,056,702 | A | 5/2000 | Lorenzo |
| 6,063,101 | A | 5/2000 | Jacobsen et al. |
| 6,063,200 | A | 5/2000 | Jacobsen et al. |
| 6,066,361 | A | 5/2000 | Jacobsen et al. |
| 6,071,305 | A | 6/2000 | Brown et al. |
| 6,106,485 | A | 8/2000 | McMahon |
| 6,106,488 | A | 8/2000 | Fleming et al. |
| 6,139,510 | A | 10/2000 | Palermo |
| 6,165,292 | A | 12/2000 | Abrams et al. |
| 6,171,296 | B1 | 1/2001 | Chow |
| 6,183,410 | B1 | 2/2001 | Jacobsen et al. |
| 6,193,686 | B1 | 2/2001 | Estrada et al. |
| 6,197,014 | B1 | 3/2001 | Samson et al. |
| 6,203,485 | B1 | 3/2001 | Urick |
| RE37,148 | E | 4/2001 | Shank |
| 6,214,042 | B1 | 4/2001 | Jacobsen et al. |
| 6,228,073 | B1 | 5/2001 | Noone et al. |
| 6,248,082 | B1 | 6/2001 | Jafari |
| 6,251,092 | B1 | 6/2001 | Qin et al. |
| 6,254,549 | B1 | 7/2001 | Ramzipoor |
| 6,260,458 | B1 | 7/2001 | Jacobsen et al. |
| 6,273,404 | B1 | 8/2001 | Holman et al. |
| 6,273,876 | B1 | 8/2001 | Klima et al. |
| 6,273,879 | B1 | 8/2001 | Keith et al. |
| 6,290,656 | B1 | 9/2001 | Boyle et al. |
| 6,296,616 | B1 | 10/2001 | McMahon |
| 6,296,631 | B2 | 10/2001 | Chow |
| 6,302,870 | B1 | 10/2001 | Jacobsen et al. |
| 6,325,790 | B1 | 12/2001 | Trotta |
| 6,338,725 | B1 | 1/2002 | Hermann et al. |
| 6,346,091 | B1 | 2/2002 | Jacobsen et al. |
| 6,352,515 | B1 | 3/2002 | Anderson et al. |
| 6,355,005 | B1 | 3/2002 | Powell et al. |
| 6,355,027 | B1 | 3/2002 | Le et al. |
| 6,368,315 | B1 | 4/2002 | Gillis et al. |
| 6,368,316 | B1 | 4/2002 | Jansen et al. |
| 6,375,628 | B1 | 4/2002 | Zadno-Azizi et al. |
| 6,375,774 | B1 | 4/2002 | Lunn et al. |
| 6,379,369 | B1 | 4/2002 | Abrams et al. |
| 6,383,146 | B1 | 5/2002 | Klint |
| 6,390,993 | B1 | 5/2002 | Cornish et al. |
| 6,398,758 | B1 | 6/2002 | Jacobsen et al. |
| 6,428,489 | B1 | 8/2002 | Jacobsen et al. |
| 6,428,512 | B1 | 8/2002 | Anderson et al. |
| 6,431,039 | B1 | 8/2002 | Jacobsen et al. |
| 6,440,088 | B1 | 8/2002 | Jacobsen |
| 6,478,778 | B1 | 11/2002 | Jacobsen et al. |
| 6,488,637 | B1 | 12/2002 | Eder et al. |
| 6,491,648 | B1 | 12/2002 | Cornish et al. |
| 6,491,671 | B1 | 12/2002 | Larson, III et al. |
| 6,503,244 | B2 | 1/2003 | Hayman |
| 6,508,803 | B1 | 1/2003 | Horikawa et al. |
| 6,524,301 | B1 | 2/2003 | Wilson et al. |
| 6,530,934 | B1 | 3/2003 | Jacobsen et al. |
| 6,547,779 | B2 | 4/2003 | Levine et al. |
| 6,553,880 | B2 | 4/2003 | Jacobsen et al. |
| 6,556,873 | B1 | 4/2003 | Smits |
| 6,579,246 | B2 | 6/2003 | Jacobsen et al. |
| 6,602,207 | B1 | 8/2003 | Mann et al. |
| 6,602,280 | B2 | 8/2003 | Chobotov |
| 6,610,046 | B1 | 8/2003 | Usami et al. |
| 6,623,448 | B2 | 9/2003 | Slater |
| 6,636,758 | B2 | 10/2003 | Sanchez et al. |
| 6,638,266 | B2 | 10/2003 | Wilson et al. |
| 6,652,508 | B2 | 11/2003 | Griffin et al. |
| 6,673,025 | B1 | 1/2004 | Richardson et al. |
| 6,682,493 | B2 | 1/2004 | Mirigian |
| 6,689,120 | B1 | 2/2004 | Gerdts |
| 6,702,762 | B2 | 3/2004 | Jafari et al. |
| 6,712,826 | B2 | 3/2004 | Lui |

(56) References Cited

U.S. PATENT DOCUMENTS

| | | |
|---|---|---|
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |
| 7,077,811 B2 * | 7/2006 | Vrba et al. .......... 600/585 |
| 7,153,277 B2 | 12/2006 | Skujins et al. |
| 7,169,118 B2 | 1/2007 | Reynolds et al. |
| 7,182,735 B2 | 2/2007 | Shireman et al. |
| 7,618,379 B2 | 11/2009 | Reynolds et al. |
| 7,850,623 B2 | 12/2010 | Griffin et al. |
| 7,878,984 B2 | 2/2011 | Davis et al. |
| 7,905,913 B2 | 3/2011 | Chew et al. |
| 7,914,466 B2 | 3/2011 | Davis et al. |
| 7,989,042 B2 | 8/2011 | Obara et al. |
| 8,021,311 B2 | 9/2011 | Munoz et al. |
| 8,048,004 B2 | 11/2011 | Davis et al. |
| 8,083,689 B2 | 12/2011 | Vrba |
| 8,113,916 B2 | 2/2012 | Miller et al. |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0116831 A1 | 6/2004 | Vrba |
| 2004/0167437 A1 | 8/2004 | Sharrow et al. |
| 2004/0167441 A1 | 8/2004 | Reynolds et al. |
| 2004/0181174 A2 | 9/2004 | Davis et al. |
| 2004/0181176 A1 | 9/2004 | Jafari et al. |
| 2005/0115624 A1 | 6/2005 | Walak |
| 2006/0264904 A1 | 11/2006 | Kerby et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0064989 A1 | 3/2008 | Chen et al. |
| 2008/0077119 A1 | 3/2008 | Snyder et al. |
| 2008/0097248 A1 * | 4/2008 | Munoz et al. .......... 600/585 |
| 2009/0043283 A1 | 2/2009 | Turnland et al. |
| 2009/0043372 A1 | 2/2009 | Northrop et al. |
| 2009/0118675 A1 | 5/2009 | Czyscon et al. |
| 2009/0177185 A1 | 7/2009 | Northrop |
| 2009/0254000 A1 | 10/2009 | Layman et al. |
| 2010/0063479 A1 | 3/2010 | Merdan et al. |

FOREIGN PATENT DOCUMENTS

| | | |
|---|---|---|
| EP | 0 778 039 | 6/1997 |
| EP | 0 937 481 | 8/1999 |
| EP | 0 790 066 | 4/2000 |
| EP | 0 608 853 | 4/2003 |
| GB | 2257269 | 1/1993 |
| JP | 58-8522 U | 1/1983 |
| JP | 62-299277 | 12/1987 |
| JP | 1-135363 A | 5/1989 |
| JP | 1-158936 A | 6/1989 |
| JP | 2-107268 A | 4/1990 |
| JP | 3-122850 | 12/1991 |
| JP | 4-061840 A | 2/1992 |
| JP | 5-506806 T | 10/1993 |
| JP | 5-309519 A | 11/1993 |
| JP | 6-312313 A | 11/1994 |
| JP | 7-124164 A | 5/1995 |
| JP | 7-124263 A | 5/1995 |
| JP | 7-136280 A | 5/1995 |
| JP | 7148264 A | 6/1995 |
| JP | 7037199 U | 7/1995 |
| JP | 7185009 A | 7/1995 |
| JP | 7275366 A | 10/1995 |
| JP | 751067 Y | 11/1995 |
| JP | 8509141 T | 10/1996 |
| JP | 8-317988 A | 12/1996 |
| JP | 9-000164 U | 4/1997 |
| JP | 9-276413 A | 10/1997 |
| JP | 10-118193 A | 5/1998 |
| JP | 2000-197704 A | 7/2000 |
| WO | WO 90/02520 | 3/1990 |
| WO | WO 95/32834 | 12/1995 |
| WO | WO 96/38193 | 12/1996 |
| WO | WO 97/44086 | 11/1997 |
| WO | WO 99/11313 | 3/1999 |
| WO | WO 02/13682 | 2/2002 |
| WO | WO 2004/047899 | 6/2004 |

* cited by examiner

MEDICAL DEVICES WITH A HEAT TRANSFER REGION AND A HEAT SINK REGION AND METHODS FOR MANUFACTURING MEDICAL DEVICES

CROSS-REFERENCE TO RELATED APPLICATION

This application claims the benefit of U.S. Provisional Application Ser. No. 61/485,750, filed May 13, 2011, the entire disclosure of which is incorporated herein by reference.

FIELD OF THE INVENTION

The present invention pertains to medical devices, and methods for manufacturing medical devices. More particularly, the present invention pertains to elongated medical devices including a slotted tubular member, components thereof, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

Embodiments of the present disclosure provide design, material, manufacturing method, and use alternatives for medical devices and tubular members for use in medical devices. An example medical device may include a guidewire. The guidewire may include a core wire having a distal portion. A tubular member may be disposed over the distal portion. The tubular member may have a plurality of slots formed therein. The tubular member may have a distal section with a heat transfer region and a heat sink region. Solder may be used to form a tip member (e.g., a solder tip member attached to the tubular member) and/or to join one or more other members at the tip of the guidewire. The solder tip member may include a portion extending through the heat transfer region of the tubular member to the heat sink region.

An example tubular member for use in a medical device may include an elongate metallic tubular body having a distal end and a lumen. A heat transfer region may be positioned adjacent to the distal end. The heat transfer region may be configured to transfer heat along the tubular body so as to promote wicking of a tip member (e.g., a solder tip member) through the lumen. A heat sink region may be positioned adjacent to the heat transfer region. The heat sink region may be configured to stop the transfer of heat along the tubular body and to define an end point for wicking of the tip member. A flexibility enhancing region may be positioned adjacent to the heat sink region. The flexibility enhancing region may have a plurality of slots formed therein.

An example method for manufacturing a medical device may include providing a tubular member having a lumen formed therein. The tubular member may have a heat transfer region defined by a distal land that is free of slots formed therein. The heat transfer region may be configured to transfer heat along the tubular member so as to promote wicking of a tip member through the lumen. The method may also include forming a heat sink region adjacent to the heat transfer region. The heat sink region may be configured to stop the transfer of heat along the tubular member and to define an end point for wicking of the tip member. The heat sink region may be defined by one or more slots formed in the tubular member. The method may also include disposing the tip member adjacent to the heat transfer region and heating the tip member. Heating the tip member may cause the tip member to wick through the lumen. When the tip member reaches the heat sink region, the tip member may cool and stop wicking through the lumen.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The devices and methods of the present disclosure may be more completely understood in consideration of the following detailed description of various embodiments in connection with the accompanying drawings, in which.

Figure 1:
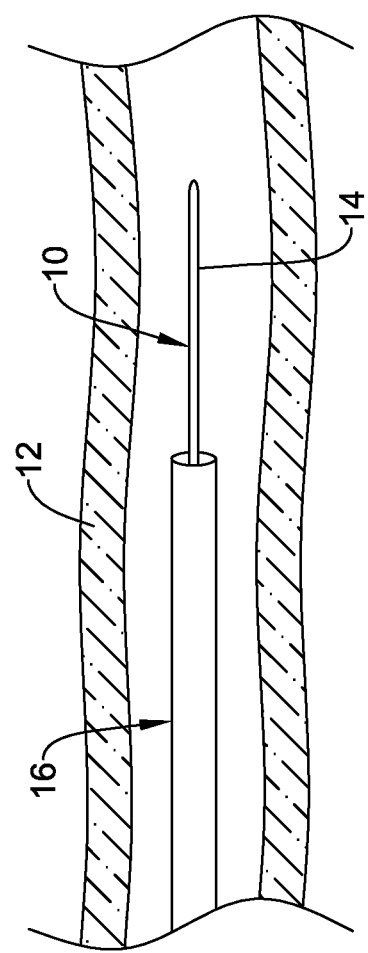
FIG. 1 is a plan view of an example medical device disposed in a blood vessel.

While the embodiments described herein are amenable to various modifications and alternative forms, specifics thereof have been shown by way of example in the drawings and will be described in detail. It should be understood, however, that the intention is not to limit the devices and methods to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
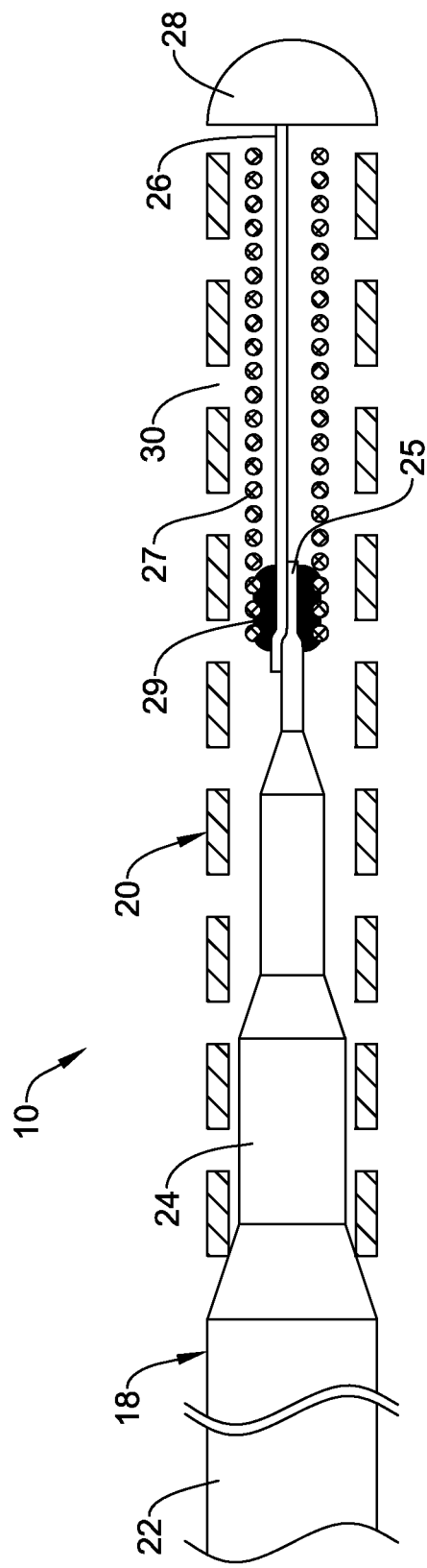
FIG. 2 is a partial cross-sectional side view of an example medical device.

FIG. 2 is a partial cross-sectional view of guidewire 10. It can be seen that guidewire 10 may include a core member or core wire 18 and a tubular member 20 disposed over at least a portion of core wire 18. Tubular member 20 may have a plurality of slots 30 formed therein. Core wire 18 may include a proximal section 22 and a distal section 24. A connector (not shown) may be disposed between and attach proximal section 22 to distal section 24. Alternatively, core wire 18 may be a unitary member without a connector. A shaping member 26 may be coupled to core wire 18 (for example distal section 24 of core wire 18), tubular member 20, or both. Shaping member 26 may be made from a relatively inelastic material so that a clinician can bend or shape the distal end of guidewire 10 into a shape that may facilitate navigation of guidewire 10 through the anatomy. Some examples of suitable materials for core wire 18, tubular member 20, shaping member 26, etc. can be found herein. A coil 27, for example a radiopaque coil, may be disposed over core wire 18 and shaping member 26. A solder bond 29 may join core wire 18, shaping member 26, and coil 27. Other joining structures and/or methods are contemplated. A tip member 28 may also be coupled to core wire 18, tubular member 20, or both that may define an atraumatic distal tip of guidewire 10. In general, tip member 28 may include solder. However, other versions of tip member 28 are contemplated including tip members 28 that comprise or form a polymeric tip.

Core wire 18, for example distal section 24 of core wire 18, may include one or more tapers or tapered sections and a flattened or stamped distal end 25. Core wire 18 may also include one or more constant outer diameter sections. The tapers or tapered sections may be formed by a number of different techniques, for example, by centerless grinding methods, stamping methods, and the like. The centerless grinding technique may utilize an indexing system employing sensors (e.g., optical/reflective, magnetic) to avoid excessive grinding of the core wire 18 section. In addition, the centerless grinding technique may utilize a CBN or diamond abrasive grinding wheel that is well shaped and dressed to avoid grabbing core wire 18 during the grinding process. In some embodiments, core wire 18 is centerless ground using a Royal Master HI-AC centerless grinder to define one or more tapered sections. In some embodiments, core wire 18 is ground using a CNC profile grinder to define one or more tapered sections.

Figure 3:
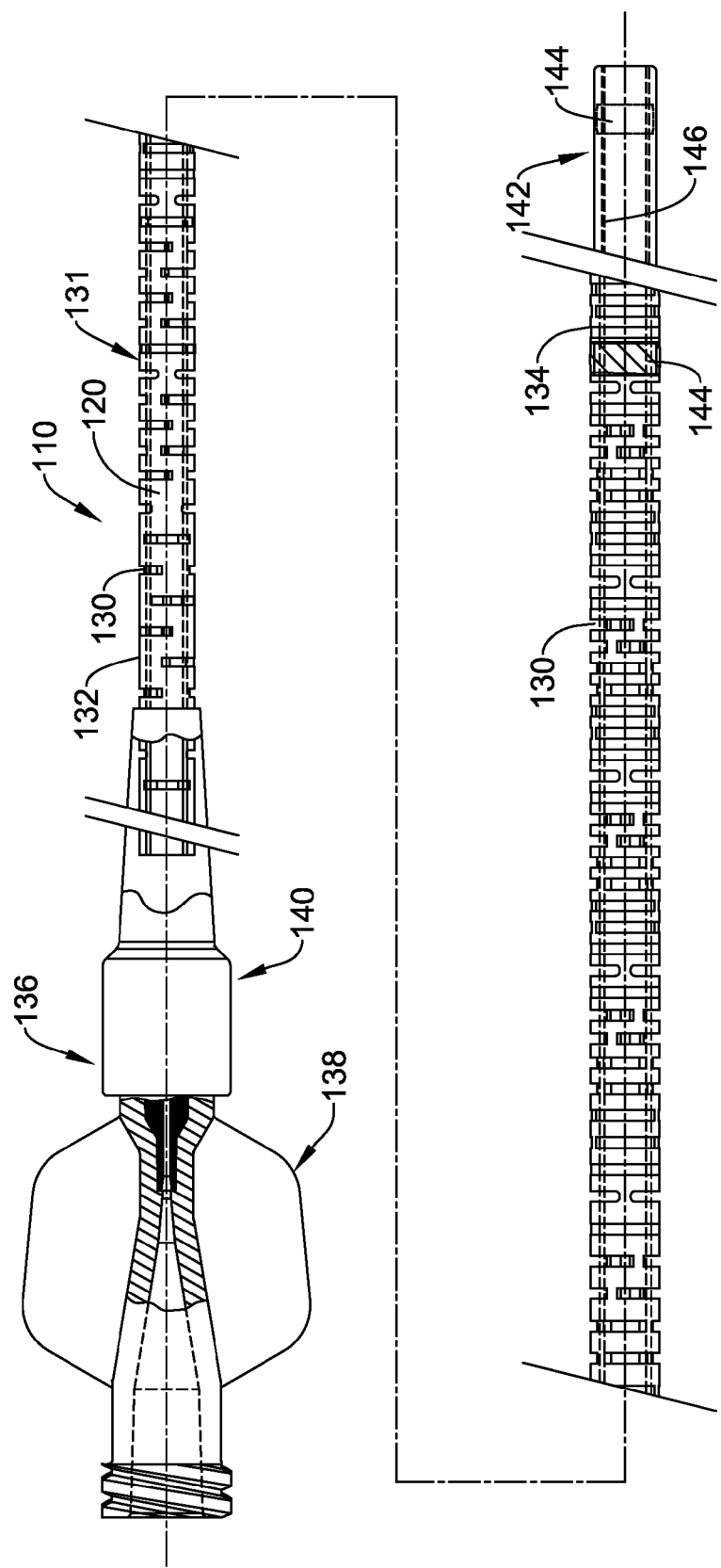
FIG. 3 is a partial cross-sectional side view of another example medical device.

Although medical device 10 is depicted in FIG. 1 as a guidewire, it is not intended to be limited to just being a guidewire. Indeed, medical device 10 may take the form of other suitable guiding, diagnosing, or treating device (including catheters, endoscopic instruments, laparoscopic instruments, etc., and the like) and it may be suitable for use at other locations and/or body lumens within a patient. For example, FIG. 3 illustrates another example device 110 in the form of a catheter. Catheter 110 may include a generally elongate shaft 131 having a proximal portion 132 and a distal portion 134. A proximal manifold 136 may be disposed at proximal portion 132. Manifold 136 may include a hub 138 and strain relief 140. A tip member 142 may be disposed at distal portion 134. Tip member 142 may include a radiopaque marker member 144. One or more additional marker members 144 may be disposed along other portions of catheter 110, for example along distal portion 134 of shaft 131. Shaft 131 may include a tubular member 120 that may be similar in form and function to other tubular members disclosed herein including tubular member 20 illustrated, for example, in FIG. 2. Tubular member 120 may have a plurality of slots 130 formed therein. A liner 146 may be disposed within tubular member 120. Liner 146 may be similar to an analogous structure disclosed in U.S. Pat. No. 7,001,369 and U.S. Patent Application Publication No. US 2006/0264904, the entire disclosures of which are herein incorporated by reference. Discussion herein pertaining to tubular member 20 and/or guidewire 10 (e.g., as illustrated in FIG. 2) may also be applicable to tubular member 120 and catheter 110, to the extent applicable.

The process of forming tip 28, for example on guidewire 10, may generally include disposing a solder ball on the end of tubular member 20 and applying heat to tubular member 20 adjacent to the solder ball (and/or to the solder ball) so that the solder ball melts. In doing so, a portion of the solder ball may wick (e.g., via capillary action) into tubular member 20 and travel along the length of tubular member 20. A portion of the solder ball remains on the distal end of the tubular member 20 and defines a generally rounded and/or atraumatic distal tip member 28. For a number of reasons it may be desirable to control the depth to which the solder wicks within tubular member 20. For example, if too little or too much solder wicks within tubular member 20, the shape and, ultimately, the atraumatic nature of tip member 28 may be undesirably altered. Accordingly, there is an ongoing need to provide methods for disposing a solder ball on tubular member 20 in order to manufacture a desirably atraumatic tip member 28.

One way to control the depth to which solder may wick within tubular member 20 is to control the transfer of heat along the length of tubular member 20. As long as enough heat is present at a particular location along tubular member 20, the solder can remain substantially molten or flowable. Once heat is no longer transferred or is otherwise dissipated, the solder will begin to solidify and stop wicking Controlling the control the transfer of heat may include the placement of heat sinks and/or carrier fixtures adjacent to the desired "end point" for solder wicking. These structures are typically designed to stop further transfer of heat along tubular member 20 so that adjacent to the carrier fixture, solder wicking can substantially cease. Other factors also can contribute to the wicking of solder within tubular member 20. For example, solder may tend to bond more reliably to metal oxide free portions of metal tubes. Thus, removal of metal oxides along the inner surface of tubular member 20 may also help to define a solder wicking end point. These are just examples.

Figure 4:
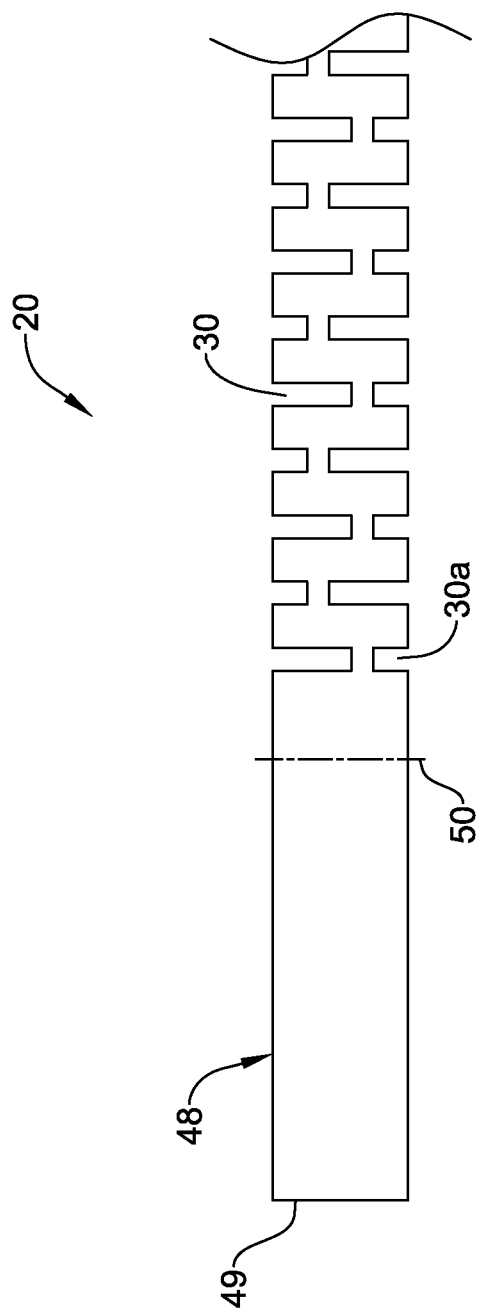
FIGS. 4-6 illustrate an example process for disposing a tip member on a distal end of an example tubular member.
Figure 5:
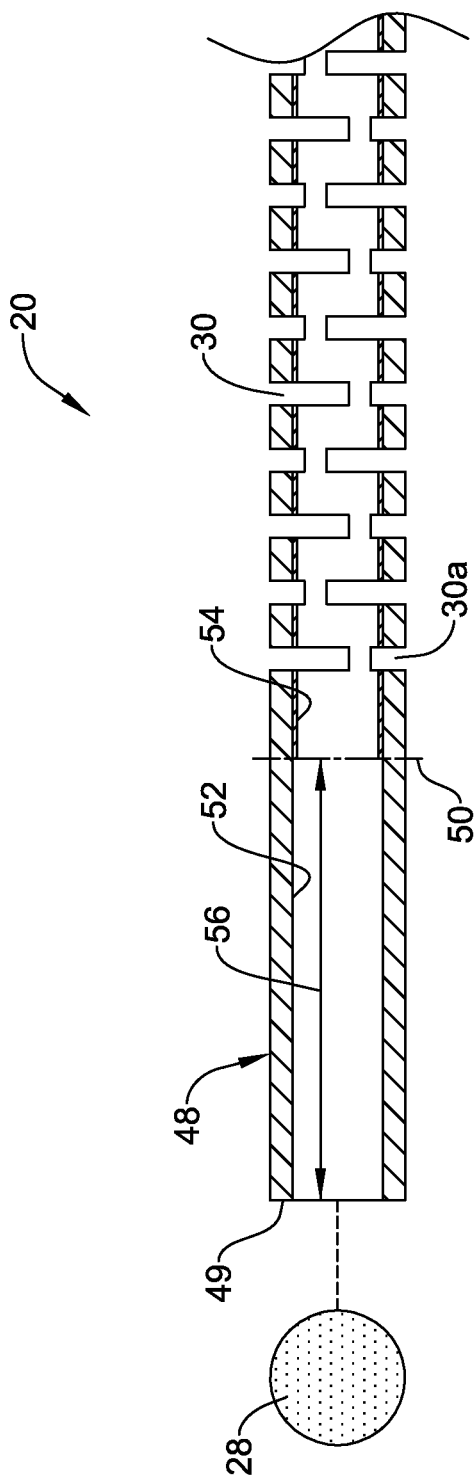
Figure 6:
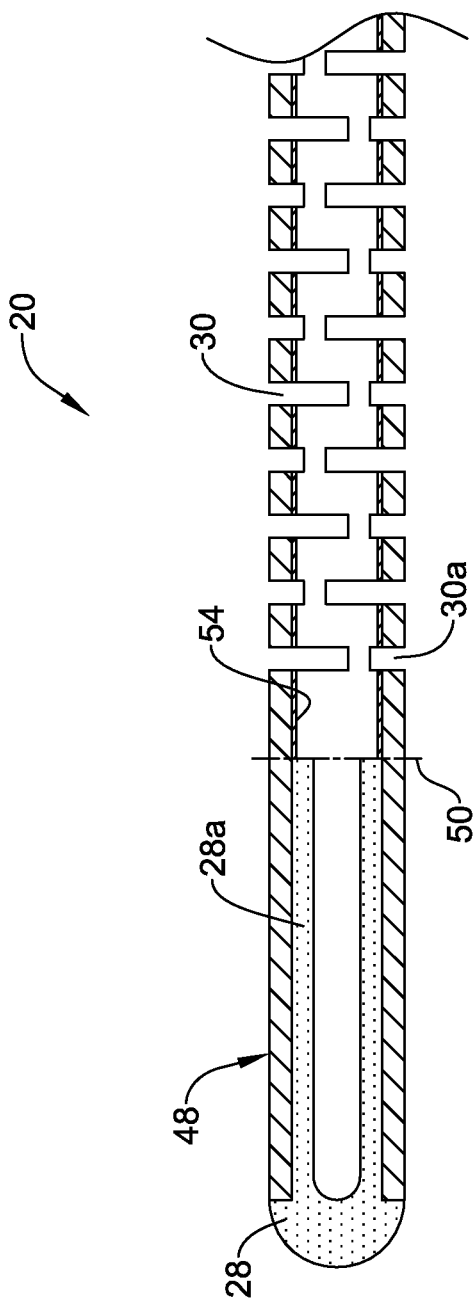

FIGS. 4-6 illustrate a process for disposing tip member 28 on tubular member 20. In FIG. 4, tubular member 20 is shown, which may include a distal land 48. Distal land 48 is generally disposed adjacent to a distal end 49 of tubular member 20 and may be characterized by the lack of slots formed therein. At a selected location along distal land 48, the solder wicking end point 50 may be defined. The position of end point 50 may be determined so that the proper amount of solder can be flowed or wick into tubular member 20 so as to define an atraumatic tip member 28. In at least some embodiments, end point 50 may be defined at a location that is spaced distally to the "first" pair or grouping of slots 30, which bears references number 30a in FIG. 5.

Heat may be applied to tubular member 20 (e.g., via a laser spot or other suitable methodologies) and the solder ball tip member 28 may be disposed on distal end 49. A portion 28a of tip member 28 may melt and wick within tubular member 20 to end point 50 as shown in FIG. 6. To aid in halting the flow of solder, several additional steps may be utilized. For example, a carrier fixture or heat sink (not shown) may be placed adjacent to end point 50 to substantially transfer heat out of tubular member 20, thereby reducing the transfer of heat along the length of tubular member 20 and allowing the solder to solidify and stop flowing. In addition, along an inner surface 52 of tubular member, metal oxides 54 may be removed (e.g., via a honing process, which may be similar to what is described in U.S. Patent Application Pub. No. US 2008/0097248, the entire disclosure of which is herein incorporated by reference) along the length 56 between distal end 49 of tubular member 20 and end point 50 as illustrated in FIG. 5. At locations proximal to the end point 50, metal oxides 54 may remain. Collectively, these processes may help to define the position of end point 50.

The use of a carrier fixture for heat dissipation may be capable of only partially diverting heat away from tubular member 20. Also, variables such as the surface finish of the carrier fixture and/or of tubular member 20, and the contact area and pressure between the carrier fixture and tubular member 20, can cause significant variability in the effectiveness of heat transfer out of tubular member 20 by the carrier fixture. This variability in heat transfer effectiveness translates directly into undesirable variability in the characteristics of the solder joint. In addition, the removal of metal oxides 54, for example via honing, may be technically challenging process. For example, precisely honing a small, highly flexible tubular structure with a rotary tool can be challenging and difficult to perform. Collectively, these challenges suggest the ongoing desirability of further refining processes for precise placement of tip member 28 onto tubular member 20.

Figure 7:
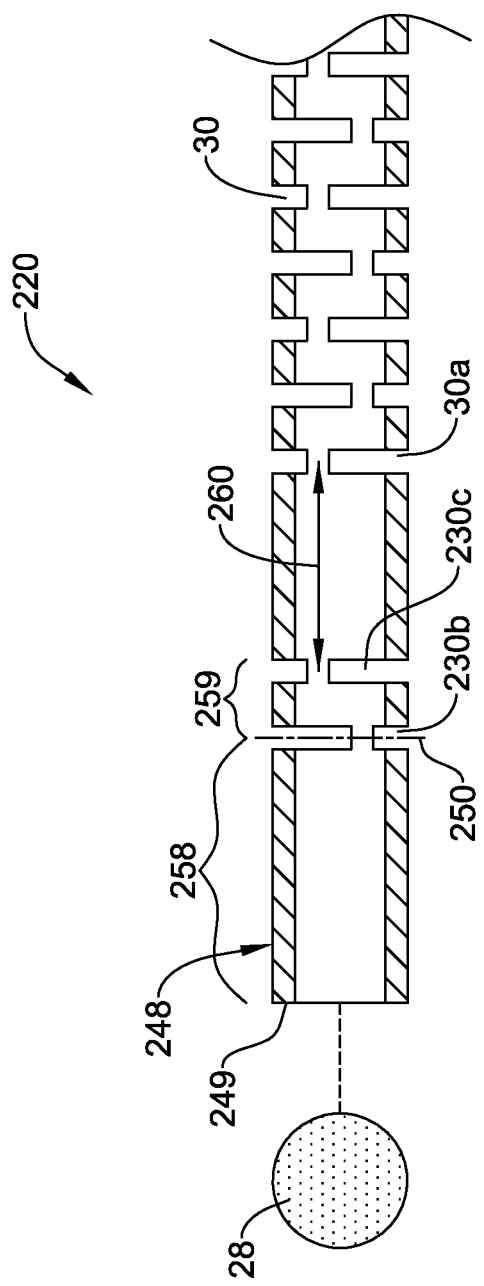
FIG. 7 illustrate another example process for disposing a tip member on a distal end of an example tubular member.

FIGS. 7, 7A, 7B, and 8 illustrate alternative processes that may be used, for example, to dispose solder onto or otherwise form tip member 28. For example, FIG. 7 illustrates tubular member 220 having slots 30 formed therein including the "first" group of slots 30a. Tubular member 228 also includes distal land 248. A heat transfer region 258 is defined along tubular member 220, for example along a portion of distal land 248. Heat transfer region 258, as the name suggests, is configured to efficiently transfer heat (e.g., heat applied at or near distal end 249) along the length of tubular member 220. Adjacent to heat transfer region 258, a heat sink region 259 is defined. Heat sink region 259, conversely to heat transfer region 258, is configured to substantially halt or otherwise attenuate the transfer of heat and define end point 250 at which solder will substantially stop wicking through tubular member 220. In other words, solder will flow through tubular member 220 to heat sink region 259 and tend to not extend proximally past heat sink region 259.

In some embodiments, heat sink region 259 is defined by a pair of slots or slot groups, for example slot groups 230b and 230c, formed in tubular member 220. For convenience, slot groups 230b/130c may be referred to as "slots" and that the "slots" and "slot groups" nomenclature can be used interchangeably for the sake of simplicity and convenience. Each or both of slot groups 230b/230c may include any suitable number, configuration, and arrangement of slots including any of the arrangements disclosed herein. For example, one or both of slots 230b/230c may be pairs of opposing slots. In other configurations, however, one or both of slots 230b/230c may include more than two slots or have other arrangements.

Slots 230b/230c may be effective in halting or otherwise attenuating the transfer of heat along tubular member 220. To help illustrate this benefit, heat transfer in tubular member 220 can be modeled with a voltage/current/resistance analogy where:

temperature differential is analogous to voltage,
heat transfer rate is analogous to current, and
thermal resistance (the inverse of thermal conductance) is analogous to electrical resistance.

Using these analogies, the thermal conductance ($T_c$) of an element of constant cross-section (e.g., tubular member 220) may be calculated as:

$$T_c = KA/L$$

where:
K is the thermal conductivity of the material,
A is the cross-sectional area of the element, and
L is the length of the element in the direction of heat transfer and/or temperature gradient.

In one specific, non-limiting example, tubular member 220 may have an outside diameter of 0.0135 inches, an inner diameter of 0.0100 inches, a wall thickness of 0.00175 inches, a cut width of 0.0007 inches, a beam height of 0.00174 inches, and a ring width of 0.00134 inches. These are just examples. In some embodiments, tubular member 220 may include a nickel-titanium alloy (e.g., nitinol). The value of K for nitinol (e.g., in the austenite form) is 18 W/m*° C. For heat transfer region 258, some example embodiments having may have the following dimensions:

$$L = 0.024 \text{ inches} = 6.1 \times 10^{-4} \text{ m, and}$$

$$A = \pi(0.0135^2 - 0.0100^2)/4 = 6.46 \times 10^{-5} \text{ in}^2 = 4.17 \times 10^{-8} \text{ m}^2.$$

Thus, the thermal resistance (which is the inverse of thermal conductance) for the heat transfer region 258 can be calculated and have a value of about 813° C./W.

Slots 230b/230c may be formed in tubular member 220 and may define heat sink region 259. Between the individual slots formed in groups 230b/230c, a set of longitudinally extending "beams" are defined by the portion of tubular member 220 remaining after tubular member 220 is cut. Using the voltage analogy, the thermal resistance at the beams defined at slots 230b can be calculated. For this first set of beams (e.g., at slots 230b) with the following example dimensions:

$$L = 0.0007 \text{ inches} = 1.8 \times 10^{-5} \text{ m, and}$$

$$A = 2 \text{ beams} * 0.00174 \text{ inches} * 0.00175 \text{ inches} = 6.09 \times 10^{-6} \text{ in}^2 = 3.93 \times 10^{-9} \text{ m}^2.$$

Thus, the thermal resistance (inverse of thermal conductance) for the first set of beams can be calculated and have a value of about 254° C./W.

After the first set of beams, a first set of rings is defined by the "ring" of material between slots 230b/230c. For the first set of rings with the following example dimensions:

$$L(\text{midwall of the ring}) = [\pi(0.0135+0.0100)/2]/2 - 0.00174 \text{ inches} = 0.0167 \text{ inches} = 4.25 \times 10^{-4} \text{ m, and}$$

$$A = 2 \text{ beams} * 0.00134 \text{ inches} * 0.00175 \text{ inches} = 4.69 \times 10^{-6} \text{ in}^2 = 3.03 \times 10^{-9} \text{ m}^2.$$

Thus, the thermal resistance (inverse of thermal conductance) for the first set of rings can be calculated and have a value of about 7792° C./W.

From these calculations, it can be appreciated that the combined thermal resistance of the first beam set and the first ring set (e.g., which may define the thermal resistance of heat sink region 259) can be calculated to be 7792+254=8046° C./W. This value is about 9.9 times greater than that of heat transfer region 258 (813° C./W). Thus, when heat is applied as a point source at distal end 249 of tubular member 220, the temperature drop across heat sink region 259 would be nearly ten times that of the temperature drop across heat transfer region 258. Collectively, these calculations indicate that the thermal conductivity can be dropped by forming heat sink region 259 in tubular member 220 and that doing so may be sufficient to stop the wicking of solder within tubular member 220.

Furthermore, in practice the application of heat (e.g., via a laser spot) may occur over roughly the distal half of heat transfer region 258, which may have the net effect of further decreasing the thermal resistance of the portion of heat transfer region 258 between the heat source and heat sink region 259, which in turn may magnify the thermal resistance effect of heat sink region 259.

Figure 8:
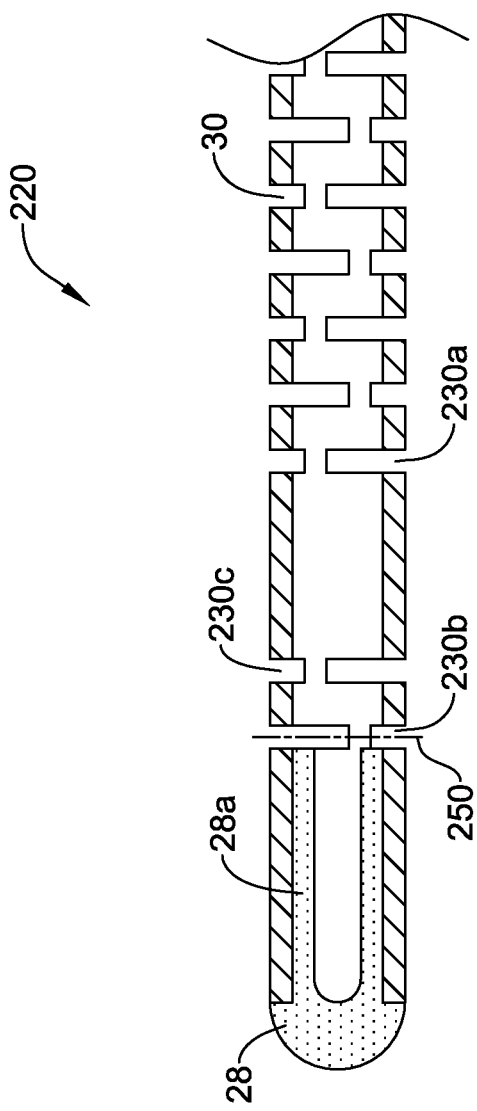
FIG. 8 further illustrates the process depicted in FIGS. 7, 7A, and 7B.

The position of end point 250 may vary. For example, in FIG. 7 end point 250 is defined at a location positioned at slots 230b. Other positions are also contemplated. For example, end point 250 may be located at slots 230c, midway between slots 230b and 230c, or other suitable locations. In either case, tip member 28 can be applied to tubular member 220 so that portion 28a of tip member 28 wicks within tubular member 220 to end point 250 as shown in FIG. 8.

Figure 7A:
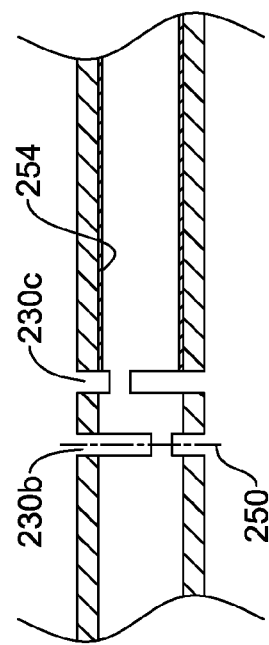
FIG. 7A is a cross-sectional side view the tubular member shown in FIG. 7.
Figure 7B:
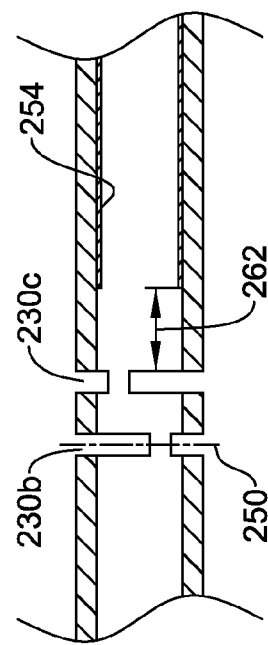
FIG. 7B is a cross-sectional side view an alternative configuration for the tubular member shown in FIG. 7.

Because heat sink region 259 helps to define end point 250, a precision metal oxide removal process may not be necessary in order to manufacture medical devices that include tubular member 220. For example, it may make little difference whether the amount of metal oxides 254 removed extends precisely to a position at slots 230c, as shown in FIG. 7A, or if the amount of metal oxides 254 removed extends further back a proximal distance 262 from slots 230C, as shown in FIG. 7B. Either way, wicking of solder may cease at end point 250. Because less precision may be required (and because the amount of metal oxide removed may no longer be directly correlated to defining end point 250), other less technically challenging methods may be used to remove metal oxides 254 such as, for example, the use of a substantially chemical process (e.g., etching) or removal of oxides with an abrasive wire or member rather than a precision drill or honing tool. This may desirably simplify the manufacturing process.

While the precise control of solder wicking in tubular member 220 has been described in the context of placement of tip member 28, this is not intended to be limiting as the controlled placement of solder may also be utilized in forming precision joints between different components of a medical device. This may include solder joints formed at a number of different locations along the length of tubular member 220 (and/or other tubular members disclosed herein). In addition, the precise positioning of solder may allow for structures to be "interlocked" with one another by the controlled placement of solder relative to other structures.

In addition to heat transfer, other method may also be used to determine the extent to which, for example, solder wicks within a tubular member. One such method is the precise application of solder flux, which aids in the bonding of solder to metallic tubular members. In other words, precise application of flux may further aid in determining where solder will wick within tubular member. Accordingly, flux application may be also be used to help define the solder wicking "end point".

Figure 9:
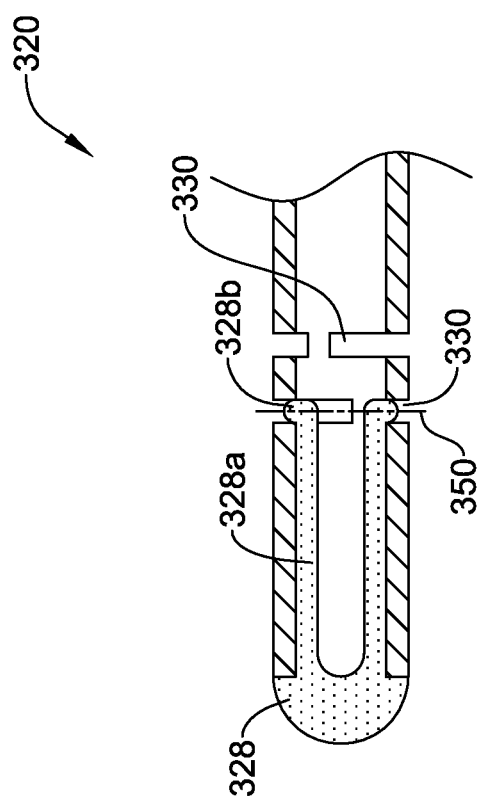
FIG. 9 is a cross-sectional side view of a portion of another example medical device.
Figure 10:
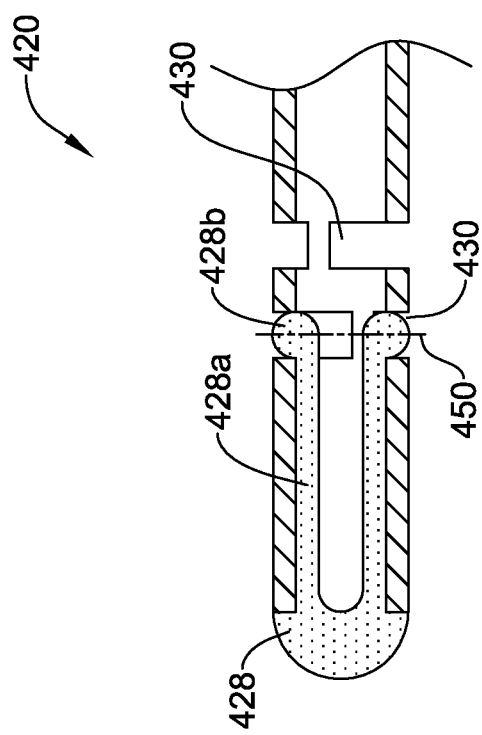
FIG. 10 is a cross-sectional side view of a portion of another example medical device.

Additionally, placement and orientation of slots in the tubular member may also help to determine the extent of wicking. This may include the use of slots as a capturing structure for capturing solder and preventing the solder from wicking past. For example, FIG. 9 illustrates tubular member 320 having slots 330 formed therein. In this example, slots 330 may capture some of the solder 328b, for example adjacent to portion 328a of tip member 328 and disrupt the capillary action of solder wicking Likewise, FIG. 10 illustrates another example tubular member 420 having slots 430 formed therein. In this example, slots 430 are wider so as to have greater solder holding capacity. Therefore, solder 428b, for example adjacent to portion 328a of tip member 328, may accumulate therein.

In still other embodiments, other methods may be used to aid in determining an end point for solder wicking. For example, portions of the tubular member may be altered so that the space or lumen defined in the tubular member is too wide to support wicking via capillary action. To achieve such an effect, the tubular member may be thinned (e.g., along the inside surface) to effectively widen the lumen. In other embodiments, the tubular member may be thinned along the outer surface. Such thinning may be constant along the length of the tubular member or may vary. The thinner portion of the tubular member may transfer heat (e.g., define a heat transfer region) and a corresponding "thicker" (and/or non-thinned) portion of the tubular member may resist further heat transfer (e.g., define a heat sink region). Other variations may include the alternative slot cut patterns (e.g., to further capture solder) or "breaks" in other structures associated with a medical device (e.g., spacing between coil windings) that may help to disrupt the capillary space by again providing a space for solder to be taken up. These are just examples and other embodiments are contemplated.

The embodiments illustrated in FIGS. 9-10 may also be described as examples where capillary action can be disrupted through the inclusion of differing slot configurations (e.g., "wide" slots 430). This disruption of capillary action may allow for precise control of not only solder through the tubular member disclosed herein but also the flow of other materials including, but not limited to, adhesives and/or bonding agents. Thus, structural arrangements similar to what is illustrated in FIGS. 9-10 can be used to aid in the precise positioning of materials such as adhesives within tubular member so as to further enhance the structural integrity of a medical device.

Various embodiments of arrangements and configurations of slots 30 are contemplated that may be used in addition to what is described above or may be used in alternate embodiments. For example, in some embodiments, at least some, if not all of slots 30 are disposed at the same or a similar angle with respect to the longitudinal axis of tubular member 20. As shown, slots 30 can be disposed at an angle that is perpendicular, or substantially perpendicular, and/or can be characterized as being disposed in a plane that is normal to the longitudinal axis of tubular member 20. However, in other embodiments, slots 30 can be disposed at an angle that is not perpendicular, and/or can be characterized as being disposed in a plane that is not normal to the longitudinal axis of tubular member 20. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 20 while still allowing for suitable torque transmission characteristics. Slots 30 may be formed such that one or more rings and/or tube segments interconnected by one or more segments and/or beams that are formed in tubular member 20, and such tube segments and beams may include portions of tubular member 20 that remain after slots 30 are formed in the body of tubular member 20. Such an interconnected structure may act to maintain a relatively high degree of torsional stiffness, while maintaining a desired level of lateral flexibility. In some embodiments, some adjacent slots 30 can be formed such that they include portions that overlap with each other about the circumference of tubular member 20. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 20 to achieve desired properties. For example, adjacent slots 30, or groups of slots 30, can be arranged in a symmetrical pattern, such as being disposed essentially equally on opposite sides about the circumference of tubular member 20, or can be rotated by an angle relative to each other about the axis of tubular member 20. Additionally, adjacent slots 30, or groups of slots 30, may be equally spaced along the length of tubular member 20, or can be arranged in an increasing or decreasing density pattern, or can be arranged in a non-symmetric or irregular pattern. Other characteristics, such as slot size, slot shape, and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section, or a distal section, or the entire tubular member 20, may not include any such slots 30.

As suggested herein, slots 30 may be formed in groups of two, three, four, five, or more slots 30, which may be located at substantially the same location along the axis of tubular member 20. Alternatively, a single slot 30 may be disposed at some or all of these locations. Within the groups of slots 30, there may be included slots 30 that are equal in size (i.e., span the same circumferential distance around tubular member 20). In some of these as well as other embodiments, at least some slots 30 in a group are unequal in size (i.e., span a different circumferential distance around tubular member 20). Longitudinally adjacent groups of slots 30 may have the same or different configurations. For example, some embodiments of tubular member 20 include slots 30 that are equal in size in a first group and then unequally sized in an adjacent group. It can be appreciated that in groups that have two slots 30 that are equal in size and are symmetrically disposed around the tube circumference, the centroid of the pair of beams (i.e., the portion of tubular member 20 remaining after slots 30 are formed therein) is coincident with the central axis of tubular member 20. Conversely, in groups that have two slots 30 that are unequal in size and whose centroids are directly opposed on the tube circumference, the centroid of the pair of beams can be offset from the central axis of tubular member 20. Some embodiments of tubular member 20 include only slot groups with centroids that are coincident with the central axis of the tubular member 20, only slot groups with centroids that are offset from the central axis of tubular member 20, or slot groups with centroids that are coincident with the central axis of tubular member 20 in a first group and offset from the central axis of tubular member 20 in another group. The amount of offset may vary depending on the depth (or length) of slots 30 and can include other suitable distances.

Slots 30 can be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 30 in tubular member 20 using these or other manufacturing steps.

In at least some embodiments, slots 30 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow tubular member 20 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form tubular member 20 without being limited by a minimum cutting blade size. Consequently, tubular members 20 may be fabricated for use in neurological devices or other devices where a relatively small size may be desired.

The materials that can be used for the various components of guidewire 10 (and/or other guidewires disclosed herein) and the various tubular members disclosed herein may include those commonly associated with medical devices. For simplicity purposes, the following discussion makes reference to tubular member 20 and other components of guidewire 10. However, this is not intended to limit the devices and methods described herein, as the discussion may be applied to other similar tubular members and/or components of tubular members or devices disclosed herein.

Tubular member 20 and/or other components of guidewire 10 may be made from a metal, metal alloy, polymer (some examples of which are disclosed below), a metal/polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®

400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, core wire 18 and/or tubular member 20, or portions thereof, may be made of a material that does not substantially distort the image and create substantial artifacts (i.e., gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example, materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using a suitable connecting technique and/or with a connector. For example, the different portions of core wire 18 can be connected using welding (including laser welding), soldering, brazing, adhesive, or the like, or combinations thereof. These techniques can be utilized regardless of whether or not a connector is utilized. The connector may include a structure generally suitable for connecting portions of a guidewire. One example of a suitable structure includes a structure such as a hypotube or a coiled wire which has an inside diameter sized appropriately to receive and connect to the ends of the proximal portion and the distal portion. Other suitable configurations and/or structures can be utilized for the connector including those connectors described in U.S. Pat. Nos. 6,918,882 and 7,071,197 and/or in U.S. Patent Pub. No. 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of guidewire 10. Alternatively, the sheath may comprise a lubricious, hydrophilic, protective, or other type of coating. Hydrophobic coatings such as fluoropolymers (e.g., PTFE) provide a dry lubricity which improves guidewire handling and device exchanges. Lubricious coatings improve steerability and improve lesion crossing capability. Suitable lubricious polymers are well known in the art and may include silicone and the like, high-density polyethylene (HDPE), hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A guidewire, comprising:
   a core wire having a distal portion; and
   a tubular member disposed over the distal portion, the tubular member having a plurality of slots formed therein;
   wherein the tubular member has a distal section with a heat transfer region and a heat sink region; and
   a solder tip member attached to a distal end of the tubular member and forming a distal tip of the guidewire, the solder tip member including a portion extending through the heat transfer region of the tubular member to the heat sink region;
   wherein the heat transfer region includes a distal land that is free of slots;
   wherein the heat sink region includes one or more slots that are designed to capture at least part of the portion of the solder tip member extending through the heat transfer region of the tubular member to the heat sink region.

2. The guidewire of claim 1, wherein the solder tip member has a proximal end, and wherein the proximal end is disposed at the heat sink region.

3. The guidewire of claim 1, wherein portions of the tubular member located proximal of the heat sink region are free of the solder tip member.

4. The guidewire of claim 1, wherein the tubular member includes a metal, and wherein the heat transfer region has an inner surface that is free of metal oxides.

5. The guidewire of claim 4, wherein a section of the inner surface of the tubular member positioned proximally of the heat sink region is free of metal oxides.

6. A tubular member for use in a medical device, the tubular member comprising:
   an elongate metallic tubular body having a distal end and a lumen;

a heat transfer region positioned adjacent to the distal end, the heat transfer region being configured to transfer heat along the tubular body so as to promote wicking of a tip member through the lumen;

a heat sink region positioned adjacent to the heat transfer region, the heat sink region begin configured to stop the transfer of heat along the tubular body and to define an end point for wicking of the tip member;

a flexibility enhancing region positioned adjacent to the heat sink region, the flexibility enhancing region having a plurality of slots formed therein;

wherein the tip member includes solder;

wherein a first portion of the solder tip member forms a distal tip on the tubular body and a second portion of the solder tip member is disposed within the lumen;

wherein the heat transfer region is defined by a distal land formed in the tubular member, the distal land being free of slots;

wherein the heat sink region is defined by one or more slots formed in the tubular body; and wherein the slots are configured to capture the tip member therein.

7. The tubular member of claim 6, wherein tubular body has an inner surface and wherein a section of inner surface extending along the heat transfer region to the heat sink region is free of metal oxides.

8. The tubular member of claim 7, wherein a proximal section of inner surface extending proximally from the heat sink region is free of metal oxides.

9. The tubular member of claim 8, wherein the proximal section of the inner surface is free of the tip member.

10. A method for manufacturing a medical device, the method comprising:

providing a tubular member having a lumen formed therein;

wherein the tubular member has a heat transfer region defined by a distal land that is free of slots formed therein, the heat transfer region being configured to transfer heat along the tubular member so as to promote wicking of a tip member through the lumen;

forming a heat sink region adjacent to the heat transfer region, the heat sink region begin configured to stop the transfer of heat along the tubular member and to define an end point for wicking of the tip member;

wherein the heat sink region is defined by one or more slots formed in the tubular member;

disposing the tip member adjacent to the heat transfer region at a distal end of the tubular member;

wherein the tip member defines a distal tip of the medical device;

heating the tip member, wherein heating the tip member causes a portion of the tip member to wick through the lumen; and wherein when the portion of the tip member that is wicking through the lumen reaches the heat sink region, the tip member cools and stops wicking through the lumen and at least part of the portion of the tip member is captured within the slots.

11. The method of claim 10, wherein the tubular member includes a metal, and further comprising honing a portion an inner surface of the tubular member to remove metal oxides disposed along the inner surface.

12. The method of claim 11, wherein the portion of the inner surface that is honed extends proximally beyond the heat sink region.

13. The method of claim 10, wherein the tubular member includes a metal, and further comprising the use of a chemical process on a portion an inner surface of the tubular member to remove metal oxides disposed along the inner surface.

* * * * *